United States Patent
Park

(10) Patent No.: US 12,024,401 B2
(45) Date of Patent: Jul. 2, 2024

(54) ESCALATOR HANDRAIL WASHING DEVICE

(71) Applicant: SWIT CO., LTD., Seoul (KR)

(72) Inventor: Kyeong Ho Park, Seoul (KR)

(73) Assignee: SWIT CO., LTD., Seoul (KR)

( * ) Notice: Subject to any disclaimer, the term of this patent is extended or adjusted under 35 U.S.C. 154(b) by 233 days.

(21) Appl. No.: 17/419,933

(22) PCT Filed: May 28, 2019

(86) PCT No.: PCT/KR2019/006377
§ 371 (c)(1),
(2) Date: Jun. 30, 2021

(87) PCT Pub. No.: WO2020/111415
PCT Pub. Date: Jun. 4, 2020

(65) Prior Publication Data
US 2022/0112053 A1  Apr. 14, 2022

(30) Foreign Application Priority Data

Nov. 28, 2018  (KR) .......................... 10-2018-0150203

(51) Int. Cl.
*B66B 31/02* (2006.01)
*A61L 2/18* (2006.01)
*H02N 1/04* (2006.01)

(52) U.S. Cl.
CPC ................ *B66B 31/02* (2013.01); *A61L 2/18* (2013.01); *A61L 2202/14* (2013.01);
(Continued)

(58) Field of Classification Search
CPC ........ B66B 31/02; A61L 2/18; A61L 2202/14; A61L 2202/15; A61L 2202/17; H02N 1/04
(Continued)

(56) References Cited

U.S. PATENT DOCUMENTS 4,976,342 A * 12/1990 Hwang .................. B65G 45/22
                                                        198/495
7,232,028 B2 * 6/2007 Schulz .................. B66B 31/003
                                                        198/321
(Continued)

FOREIGN PATENT DOCUMENTS

CN        207774584 U    8/2018
JP        10-036055 A    2/1998
(Continued)

OTHER PUBLICATIONS

US 2023/0117313 A1, Wang, Apr. 20, 2023.*

*Primary Examiner* — Douglas A Hess
(74) *Attorney, Agent, or Firm* — NKL Law; Jae Youn Kim

(57) ABSTRACT

An escalator handrail washing device according to one embodiment of the present invention comprises: a case that accommodates an escalator handrail and a washing unit; a self-generation unit, arranged in the case, for converting kinetic energy of the escalator handrail into electric energy; and a communication unit for transferring information on an operating state of the escalator handrail to a control center. The washing unit includes a plurality of rollers. At least one roller is rotated without power, by frictional force generated by contacting a surface of the escalator handrail, in a first direction which is a reverse direction of a preset rotating direction of the escalator handrail. Other rollers are rotated by rotational force of the at least one roller. The other rollers can sterilize or wash the escalator handrail while rotating.

7 Claims, 6 Drawing Sheets

(52) U.S. Cl.
CPC ....... *A61L 2202/15* (2013.01); *A61L 2202/17* (2013.01); *H02N 1/04* (2013.01)

(58) Field of Classification Search
USPC .................................................. 198/322, 495
See application file for complete search history.

(56) References Cited

U.S. PATENT DOCUMENTS

| | | | |
|---|---|---|---|
| 7,854,313 B1 * | 12/2010 | Gotsche | B66B 31/02 |
| | | | 198/495 |
| 8,573,385 B2 * | 11/2013 | Yun | B66B 31/003 |
| | | | 198/321 |
| 9,415,128 B2 * | 8/2016 | Yukimoto | A61L 2/18 |
| 9,415,129 B2 * | 8/2016 | Yukimoto | B66B 31/02 |
| 9,856,116 B2 * | 1/2018 | Ibrahim | B66B 31/02 |
| 10,160,622 B2 * | 12/2018 | Kim | A61L 2/08 |
| 11,174,131 B1 * | 11/2021 | Gonzalez | A61L 2/10 |

FOREIGN PATENT DOCUMENTS

| | | |
|---|---|---|
| JP | H10338449 A | 12/1998 |
| JP | 2008063103 A | 3/2008 |
| JP | 2008280141 A | 11/2008 |
| KR | 10-2011-0016145 A | 2/2011 |
| KR | 10-2015-0098342 A | 8/2015 |
| KR | 10-1663602 B1 | 10/2016 |
| KR | 10-2017-0073913 A | 6/2017 |

* cited by examiner

ESCALATOR HANDRAIL WASHING DEVICE

TECHNICAL FIELD

The following embodiments relate to an apparatus for washing a handrail of an escalator.

BACKGROUND ART

In general, an escalator is a representative vertical transportation means together with an elevator. The escalator has superior transport capacity (6,000 people/hr to 9,000 people/hr, about 10 times higher than the elevator) than the elevator to transport many passengers in a short time. Thus, the escalator is mainly installed in places at which people frequently pass, such as department stores, large buildings, hotels, subways, and airports, in particular, the use of the escalator is rapidly increasing as the number of large discount stores is rapidly increasing in recent years.

The escalator as described above transports people while stairs move, and people have to hold a handrail for the safety of passengers and also hold the handrail of the escalator at the same time as boarding for safety reason.

The typical escalator is configured to include a step for transporting passengers while being circulated along a predetermined track, a handrail installed on both sides of the step to serve as a handle, and a driving device for driving the step and the handrail.

In the escalator configured as described above, when the driving device operates, the step and the handrail are circulated along a predetermined track at a predetermined speed to transport passengers. Therefore, passengers boarding on the escalator may safely move to their destinations if holding only the handrail.

The handrail provided on the escalator is a means for preventing safety accidents that may occur when using the escalator and is inevitable to be contact with hands of many passengers. Therefore, it has the same problems as listed below for hygiene reasons. First, a surface of the handrail is easily dirty by various foreign substances such as sweat secreted from the passenger's hands, which is not good in outer appearance. Second, since the handrail is in contact with the hands of many passengers, contamination due to bacteria is serious.

For reference, in view of the handrail and toilet bowl, contrary to the general idea that the toilet bowl is more contaminated, the severity of the results may be seen from the results of the investigation, in which a greater number of bacteria is detected on the handrail.

Various methods have been devised to solve such a problem, and one of the most used methods is a method in which an operator directly wash the handrail using a detergent and a cloth.

However, since this method is performed manually, efficiency thereof is inevitably reduced, and inconspicuous portions out of sight of the operator are easily overlooked. In addition, since this method is merely a work at a level of simply removing the foreign substances, a sterilization effect may not be expected at all, and there is a problem in that the bacteria remain as they are although it look clean when viewed with the naked eye.

An escalator handrail cleaner is disclosed in Korean Patent Publication No. 2009-0080655 (Published on Aug. 28, 2009).

DISCLOSURE OF THE INVENTION

Technical Problem

An object according to one embodiment is to provide an apparatus for washing a handrail of an escalator, which is capable of operating without power by frictional force with the handrail when the handrail of the escalator rotates.

An object according to an embodiment is to provide an apparatus for washing a handrail of an escalator, which is capable of preventing a safety accident from occurring by transmitting information to a control center, when reverse rotation of the handrail is detected through a sensor capable of the reverse rotation of the handrail, while washing the handrail of the escalator.

An object according to one embodiment is to provide an apparatus for washing a handrail of an escalator, which is capable of performing smooth washing on handrails of various types of escalators because of being elastically adjusted in position by an elastic element.

Technical Solution

An apparatus for washing a handrail of an escalator according to an embodiment includes a case configured to accommodate the handrail of the escalator and a washing part, a self-generation part disposed in the case to convert kinetic energy of the handrail of the escalator into electric energy, the washing part configured to wash the handrail of the escalator, a control part configured to control the handrail of the escalator, and a communication part configured to transmit information on an operation state of the handrail of the escalator to a control center, and the washing part includes a plurality of rollers.

At least one roller may rotate without power in a first direction that is opposite to a preset rotation direction of the handrail of the escalator by friction force generated by being in contact with a surface of the handrail of the escalator, and other rollers may rotate by rotational force of the at least one roller to disinfect and wash the handrail of the escalator while the other rollers rotate.

A first sensor element configured to detect a rotation direction of the at least one roller may be disposed at one side of the at least one roller, and when the first sensor element detects the rotation of the at least one roller in the first direction, the control part may determine that an operation of the escalator is normal, when the first sensor element detects that the at least one roller does not rotate, the control part may determine that the operation of the escalator is abnormal, and when the first sensor element detects that the at least one roller is rotating in a second direction that is opposite to the first direction, the control part may determine that the operation of the escalator is abnormal.

In addition, when the control part determines that the operation of the escalator is abnormal, a warning sound may be generated by itself. Alternatively, in this case, the communication part may warn the control center that the handrail of the escalator is rotating in the reverse direction with respect to the preset rotation direction.

The washing part may include a first roller rotating without the power in the first direction by the frictional force generated by being in contact with the surface of the handrail of the escalator, a second roller rotating in the second direction that is opposite to the first direction by the rotational force of the first roller to remove and disinfect foreign substances of the handrail by using a disinfectant solution sprayed onto the surface, a third roller rotating in the first direction by the rotational force of the first roller to wash the disinfectant solution adhering to the surface of the handrail, and a fourth roller rotating in the second direction by the rotational force of the first roller to rewash the disinfectant solution remaining on the surface of the handrail, wherein the first sensor element may be disposed at one side of the first roller.

The washing part may further include a frame configured to accommodate the first to fourth rollers, and a plurality of holes may be sequentially formed in each of both side surfaces of the frame, and the first to fourth rollers are detached to the holes formed in both the side surfaces of the frame by a rotation shaft passing through each of the rollers, respectively.

The apparatus may further include an elastic element disposed below the frame of the washing part so as to be connected to the frame, wherein the washing part may move elastically upward or downward by the elastic element so that the first to fourth rollers are in contact with the surface of the handrail of the escalator.

The apparatus may further include a first elastic element connected to a portion, at which the first roller is disposed, on the frame, and a second elastic element connected to a portion, at which each of the second to fourth rollers is disposed, on the frame.

The control part may control the first elastic element so that elastic force of the first elastic element corresponds to a first preset pressure that is set so that the first roller and the surface of the handrail of the escalator are in close contact with each other.

In addition, the control part may control the second elastic element so that the elastic force of the second elastic element corresponds to a second preset pressure set so that the second to fourth rollers and the surface of the handrail of the escalator are in contact with each other.

A second sensor element capable of detecting a concentration of the disinfectant solution remaining on the surface of the second roller may be disposed on a portion of the surface of the first roller, the control part may control an amount of disinfectant solution sprayed onto the surface of the second roller, and the control part may control the amount of disinfectant solution sprayed onto the surface of the second roller, based on the concentration of the disinfectant solution detected by the second sensor element.

The self-generation part may include a power generation element configured to convert the kinetic energy of the handrail of the escalator into the electric energy while rotating by the frictional force generated by being in contact with the surface of the handrail of the escalator, a charging element configured to store the electric energy generated by the power generation element, and a moving element capable of moving a position of the power generation element so that the power generation element is in contact with the surface of the handrail of the escalator, wherein the power generation element may rotate about one axis by the moving element.

The disinfectant solution sprayed onto the surface of the second roller may be alcohol or chlorine dioxide.

Advantageous Effects

The apparatus for washing the handrail of the escalator according to an embodiment may operate without the power by the frictional force with the handrail when the handrail of the escalator rotates.

The apparatus for washing the handrail of the escalator according to an embodiment may prevent the safety accident from occurring by transmitting the information to the control center when the reverse rotation of the handrail is detected through the sensor capable of the reverse rotation of the handrail, while washing the handrail of the escalator.

The apparatus for washing the handrail of the escalator according to an embodiment may perform the smooth washing on the handrails of various types of escalators because of being elastically adjusted in position by the elastic element.

MODE FOR CARRYING OUT THE INVENTION

Figure 1:
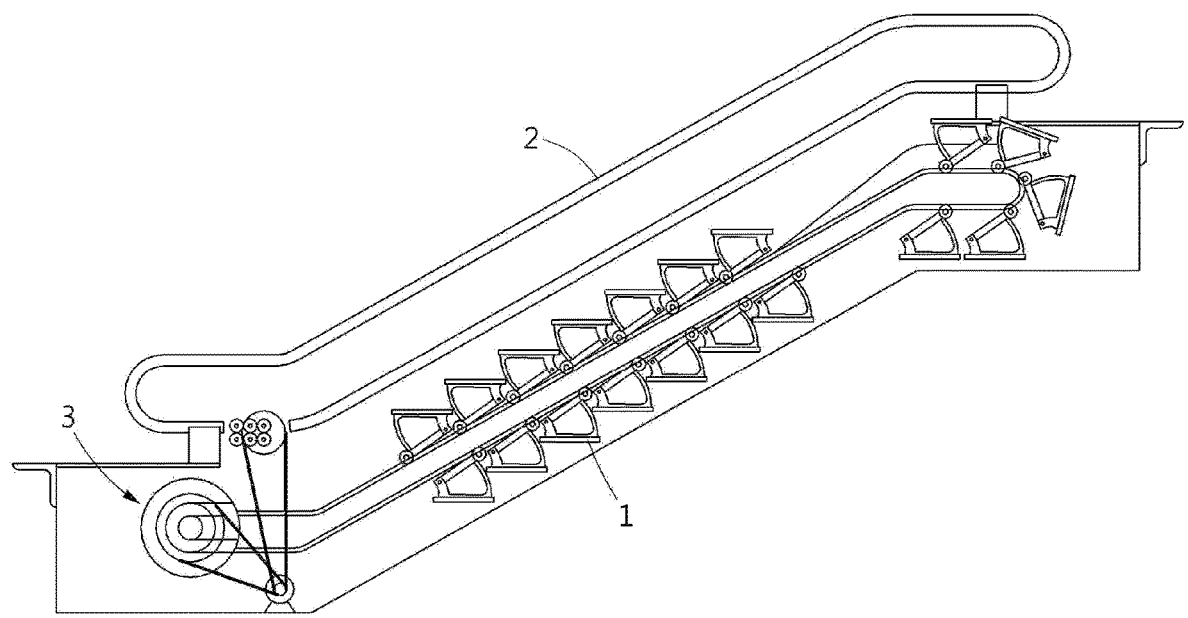
FIG. 1 is a schematic view of a typical escalator.

Hereinafter, embodiments will be described in detail with reference to the accompanying drawings. The following description is one of several aspects of the embodiments, and the following description constitutes a portion of detailed description of the embodiments.

However, in descriptions of the present invention, detailed descriptions related to well-known functions or configurations will be ruled out in order not to unnecessarily obscure subject matters of the present invention.

In addition, based on the principle that terms or words used in the specification and claims should not be construed as a lexical meaning, and should be understood as appropriate notions by the inventor based on that he/she is able to define terms to describe his/her invention in the best way to be seen by others, it should be interpreted as meaning and concept consistent with the technical idea of the escalator handrail washing device according to an embodiment.

Thus, the embodiment described in this specification and the configuration shown in the drawings are only the most preferred embodiment of an apparatus for washing a handrail of an escalator according to an embodiment, and all of the technical ideas of the apparatus for washing the handrail of the escalator according to an embodiment are not represented and should be understood that there may be various equivalents and modifications capable of being substituted for them at the time of filing the present application.

Figure 2:
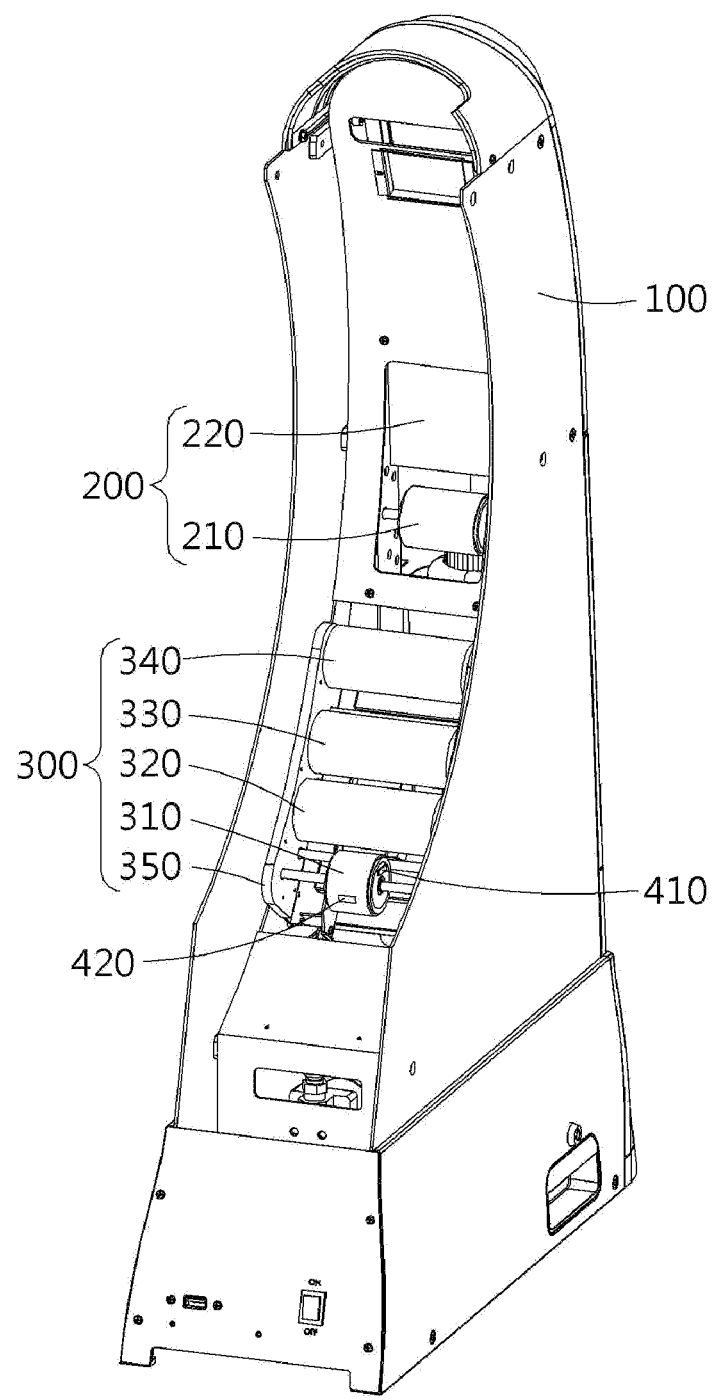
FIG. 2 is a perspective view illustrating an apparatus for washing a handrail of an escalator according to an embodiment.
Figure 3:
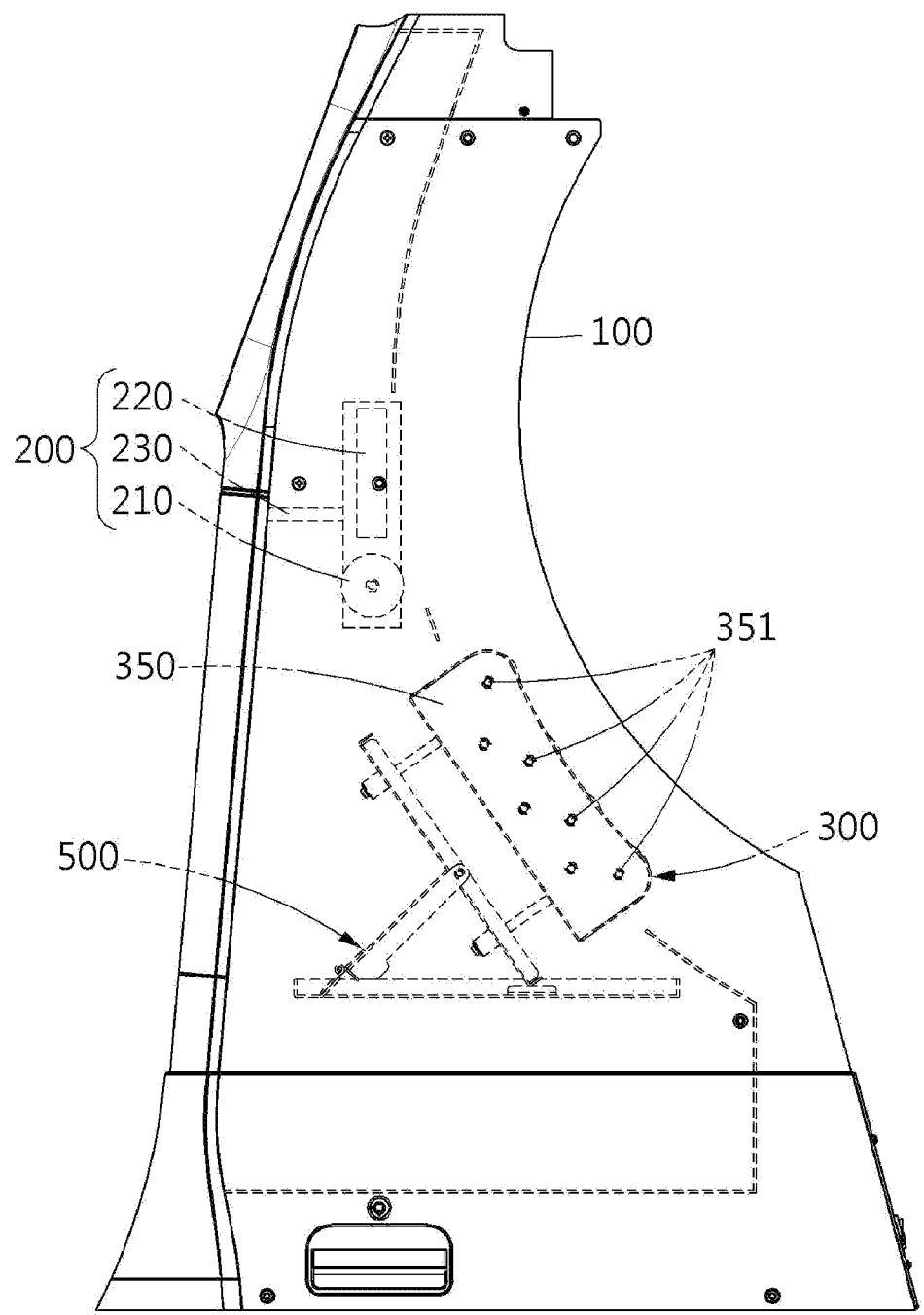
FIG. 3 is a see-through view illustrating a side surface of the apparatus for washing the handrail of the escalator according to an embodiment.

FIG. 1 is a schematic view of a typical escalator. FIG. 2 is a perspective view illustrating an apparatus for washing a handrail of an escalator according to an embodiment. FIG. 3 is a see-through view illustrating a side surface of the apparatus for washing the handrail of the escalator according to an embodiment.

Figure 4:
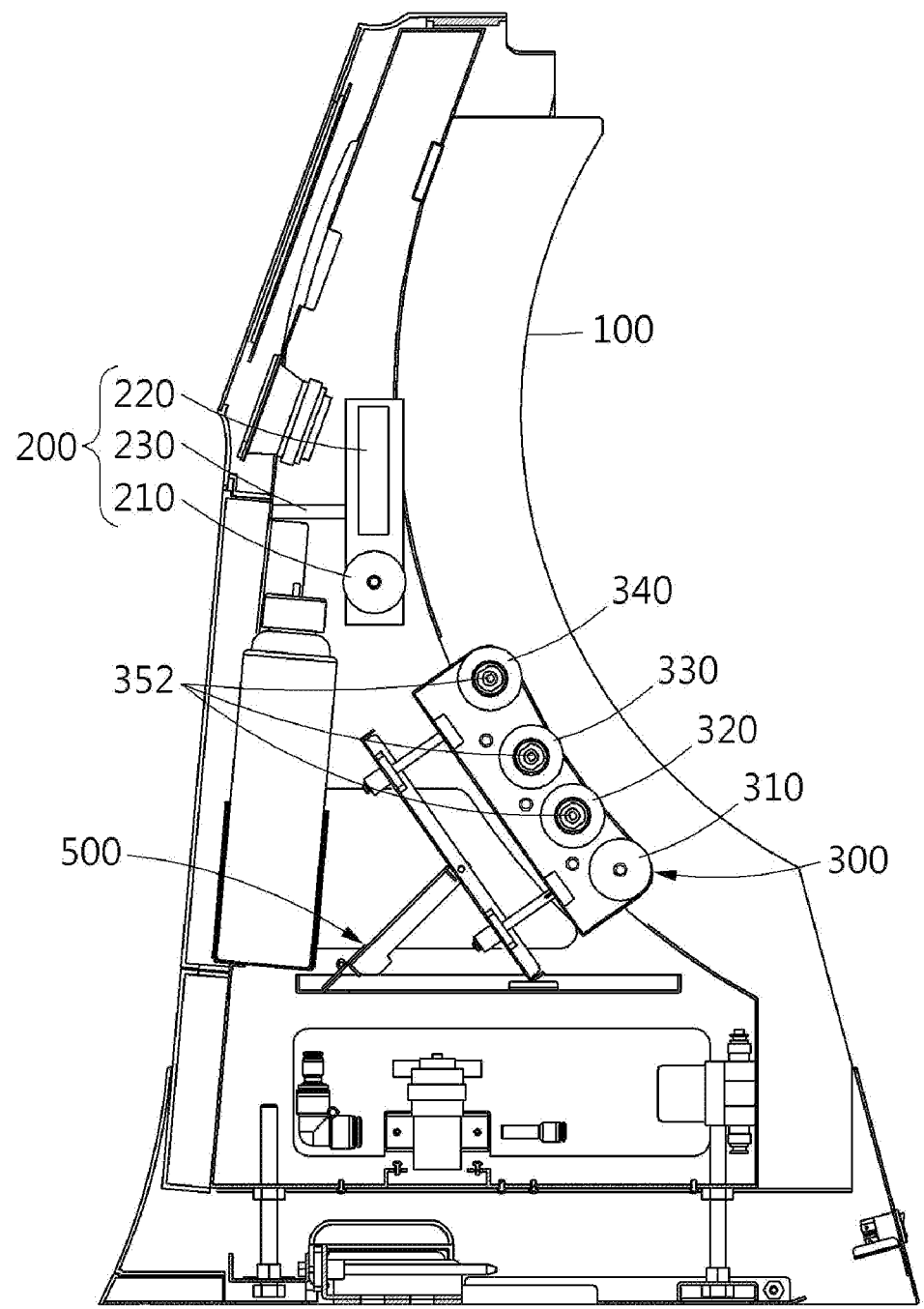
FIG. 4 is a see-through view illustrating a side surface of a washing part of the apparatus for washing the handrail of the escalator according to an embodiment.
Figure 5:
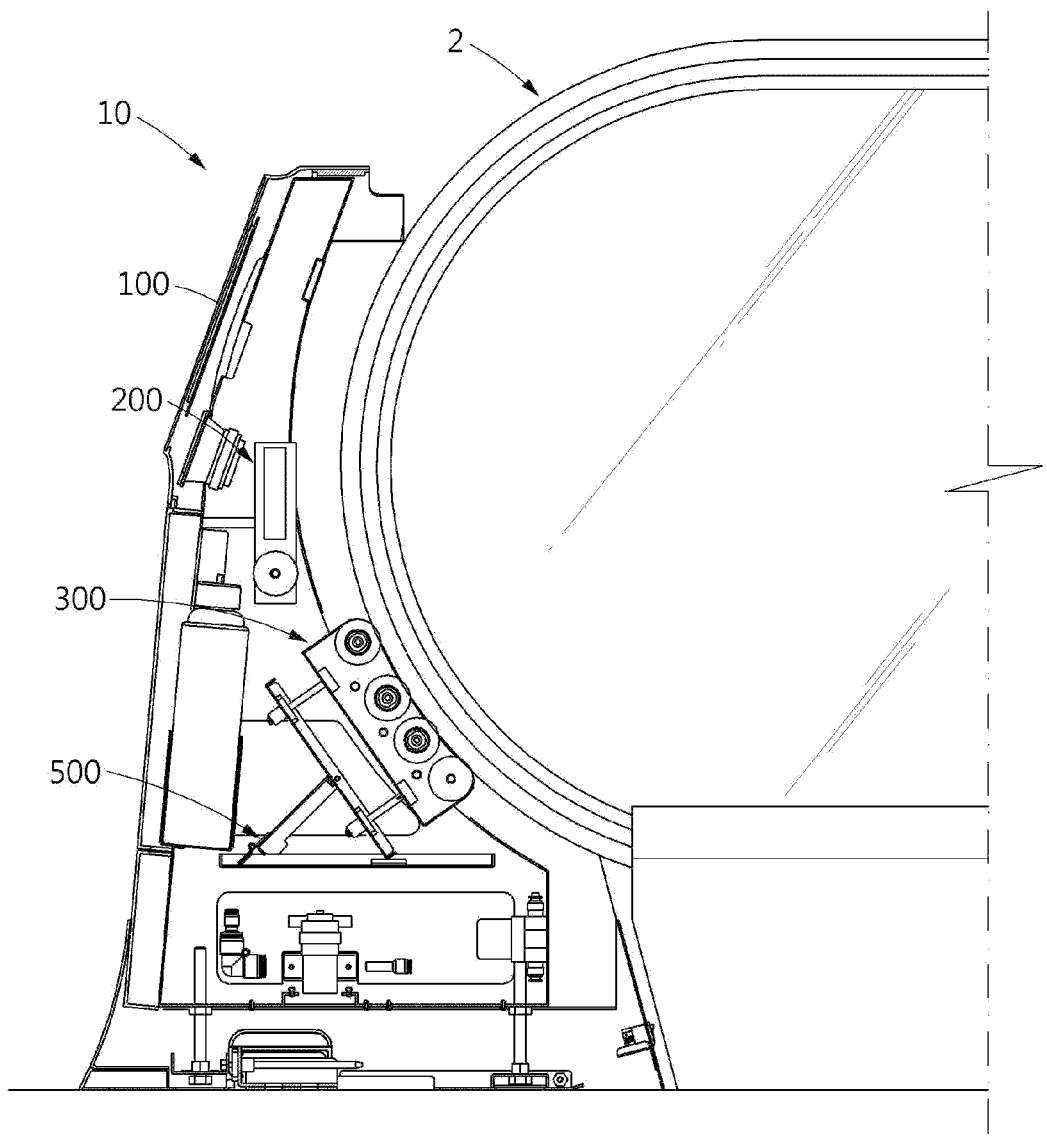
FIG. 5 is a view illustrating a state in which the apparatus for washing the handrail of the escalator is mounted on an escalator according to an embodiment.

FIG. 4 is a see-through view illustrating a side surface of a washing part of the apparatus for washing the handrail of the escalator according to an embodiment. FIG. 5 is a view illustrating a state in which the apparatus for washing the handrail of the escalator is mounted on an escalator according to an embodiment.

Figure 6:
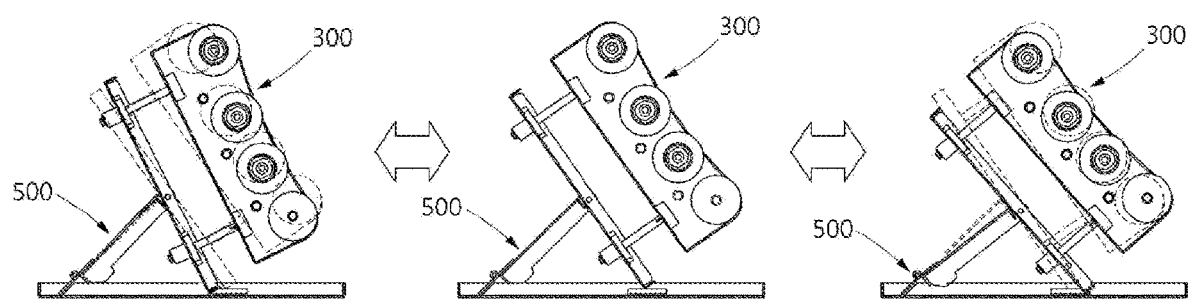
FIG. 6 is a view illustrating an operation state of the apparatus for washing the handrail of the escalator according to an embodiment.

FIG. 6 is a view illustrating an operation state of the apparatus for washing the handrail of the escalator according to an embodiment.

Referring to FIG. 1, a typical escalator includes a step 1 that transports passengers while being circulated along a predetermined track, a handrail 2 installed on both sides of the step 1 to serve as a handle, and a driving device 3 that drives the step 1 and the handrail 2.

Here, an apparatus for washing a handrail of an escalator according to an embodiment is disposed at one side of the escalator to wash and disinfect a surface of the handrail.

Referring to FIG. 2, an apparatus 10 for washing a handrail of an escalator according to an embodiment includes a case 100 configured to accommodate the handrail of the escalator and a washing part 300, a self-generation part 200 disposed in the case 100 to convert kinetic energy of the handrail of the escalator into electric energy, the washing part 300 configured to wash the handrail of the escalator, a control part (not shown) configured to control the apparatus 10 for washing the handrail of the escalator, and a communication part (not shown) configured to transmit information on an operation state of the handrail of the escalator to a control center, and the washing part 300 includes a plurality of rollers.

At this time, at least one roller may rotate without power in a first direction that is opposite to a preset rotation direction of the handrail of the escalator by the friction force generated by being in contact with the surface of the handrail of the escalator. Also, other rollers may rotate by rotational force of the at least one roller to disinfect and wash the handrail of the escalator while the other rollers rotate.

Specifically, the washing part 300 includes a friction roller 310 that is in contact with the surface of the handrail of the escalator to rotate by receiving driving force from the handrail of the escalator and a least one washing roller 320 or 330 that receives the driving force from the friction roller 310 to rotate.

An outer circumferential surface of the friction roller 310 may be preferably made of a material having high frictional force with the surface of the handrail so that the driving force is capable of being transmitted from the surface of the handrail in a state of being in contact with the surface of the handrail of the escalator, and the outer circumferential surface of the friction roller 310 may be made of a resin material such as rubber.

Furthermore, the outer circumferential surface of the friction roller 310 may include a plurality of unevennesses or friction protrusions to increase in frictional force with the surface of the handrail of the escalator and also may include a plurality of uneven mountains parallel to a rotation shaft of the friction roller 310.

The at least one washing roller 320 may also rotate in the state of being in contact with the surface of the handrail of the escalator to perform washing on the surface of the handrail of the escalator.

However, it is preferable that the washing roller 320 has frictional force with the surface of the handrail, which is less than the frictional force of the friction roller 310 so as to smoothly wash the handrail of the escalator.

As described above, the at least one washing roller 320 or 330 may rotate by receiving the driving force from the friction roller 310, and rotating shafts of the washing rollers 320 and 330 and the rotating shaft of the friction roller 310 may be connected through a power transmission member, and thus, the washing rollers 320 and 330 may rotate together by the rotation of the friction roller 310.

As described above, the washing part 300 itself may operate without the power without supply of separate power.

Furthermore, a spray part configured to spray a washing solution to the washing roller 320 may operate by the driving force of the friction roller 310. That is, the spray part configured to spray the washing solution may also operate without the power without a separate power source.

In addition, a first sensor element 410 configured to detect a rotation direction of the at least one roller may be disposed at one side of the at least one roller. That is, the first sensor element 410 configured to detect the rotation direction of the friction roller 310 may be disposed at one side of the friction roller 310.

When the first sensor element 410 detects the rotation of the at least one roller 310 in the first direction, the control part may determine that the operation of the escalator is normal, and when the first sensor element 410 detects that the at least one roller 310 does not rotate, the control part may determine that the operation of the escalator is abnormal. Also, when the first sensor element 410 detects that the at least one roller 310 is rotating in a second direction opposite to the first direction, the control part may determine that the operation of the escalator is abnormal.

In addition, when the control part determines that the operation of the escalator is abnormal, a warning sound may be generated by itself. Alternatively, in this case, the communication part may warn the control center that the handrail of the escalator is rotating in the reverse direction with respect to the preset rotation direction.

That is, when the handrail rotates in the direction opposite to the preset direction for the normal operation, the at least one roller also rotates in the second direction, not the first direction, which is the conventional rotation direction. At this time, such a situation may be recognized immediately by the first sensor element 410, and the communication part may promptly transmit this information to the control center to protect the safety of passengers, and also, the control center may stop the operation of the escalator.

As an example, the washing part 300 may include a first roller 310 (friction roller) rotating without the power in the first direction by the frictional force generated by being in contact with the surface of the handrail of the escalator, a second roller 320 (washing roller) rotating in the second direction that is opposite to the first direction by the rotational force of the first roller to remove and disinfect foreign substances of the handrail by using a disinfectant solution sprayed onto the surface, a third roller 330 (washing roller) rotating in the first direction by the rotational force of the first roller 310 to wash the disinfectant solution adhering to the surface of the handrail, and a fourth roller 340 (washing roller) rotating in the second direction by the rotational force of the first roller 310 to rewash the disinfectant solution remaining on the surface of the handrail, and the first sensor element 410 may be disposed at one side of the first roller 310.

In addition, a second sensor element 420 capable of detecting a concentration of the disinfectant solution remaining on the surface of the second roller 320 may be disposed on a portion of the surface of the first roller 310. In addition, the control part may control an amount of disinfectant solution sprayed onto the surface of the second roller 320. Thus, the control part may control the amount of disinfectant solution sprayed onto the surface of the second roller 320, based on the concentration of the disinfectant solution detected by the second sensor element 420.

Furthermore, the self-generation part 200 may include a power generation element 210 configured to convert the kinetic energy of the handrail of the escalator into the electric energy while rotating by the frictional force generated by being in contact with the surface of the handrail of the escalator, a charging element 220 configured to store the electric energy generated by the power generation element 210, and a moving element 230 capable of moving a position of the power generation element so that the power generation element 210 is in contact with the surface of the handrail of the escalator, and the power generation element 210 may rotate about one axis by the moving element 230.

Referring to FIGS. 3 and 4, the washing part 300 may further include a frame 350 configured to accommodate the first to fourth rollers, and a plurality of holes 351 may be sequentially formed in each of both side surfaces of the frame. In addition, the first to fourth rollers may be detached to the holes 351 formed in both the side surfaces of the frame by a rotation shaft 352 passing through each of the rollers, respectively.

In addition, the apparatus for washing the handrail of the escalator may further include an elastic element 500 disposed below the frame 350 of the washing part 300 so as to be connected to the frame, and the washing part 300 may move elastically upward or downward by the elastic element 500 so that the first to fourth rollers are in contact with the surface of the handrail of the escalator.

Furthermore, the disinfectant solution sprayed onto the surface of the second roller 420 may be alcohol or chlorine dioxide for effective and safe disinfection and washing. However, the present invention is not limited thereto, and it is obvious that a material that is capable of being very easily derived by the respective of those skilled in the art may be used as the disinfectant solution.

Referring to FIG. 5, the apparatus 10 for washing the handrail of the escalator may be mounted on the handrail 2 of the escalator to operate. At this time, when the handrail 2 rotates, the washing part 300 may wash the handrail 2 while operating without the power by the rotation of the handrail 2. In addition, the power generation element 210 of the self-generation part 200 may also generate electric energy while rotating by frictional force when the handrail 2 rotates and then store the electric energy in the charging element 220.

Furthermore, as illustrated in FIG. 6, regardless of the type of the escalator handrail 2 to be mounted, the washing part 300 may move by the elastic element 500 and then be disposed at an optimal position for disinfecting and washing the handrail 2 of the escalator.

Specifically, the apparatus for washing the handrail of the escalator may further include a first elastic element connected to a portion, at which the first roller is disposed, on the frame and a second elastic element connected to a portion, at which each of the second to fourth rollers is disposed, on the frame.

Furthermore, the control part may control the first elastic element so that elastic force of the first elastic element corresponds to a first preset pressure that is set so that the first roller and the surface of the handrail of the escalator are in close contact with each other.

Also, the control part may control the second elastic element so that the elastic force of the second elastic element corresponds to a second preset pressure set so that the second to fourth rollers and the surface of the handrail of the escalator are in contact with each other.

The first and second elastic elements described above may include separate driving parts so that the first to fourth rollers are in close contact with the surface of the handrail of the escalator at the first and second preset pressures. For example, each of the first and second elastic elements may include a component such as a piston or a solenoid, and thus, the first to fourth rollers are elastically manipulated to be in close contact with the surface of the handrail of the escalator at the first and second preset pressures through an operation of the piston or solenoid.

The apparatus for washing the handrail of the escalator, which has the above-described configuration, may operate without the power by the frictional force with the handrail when the handrail of the escalator rotates.

In addition, the apparatus for washing the handrail of the escalator may prevent the safety accident from occurring by transmitting the information to the control center when the reverse rotation of the handrail is detected through the sensor capable of the reverse rotation of the handrail, while washing the handrail of the escalator.

Furthermore, the apparatus for washing the handrail of the escalator may perform the smooth washing on the handrails of various types of escalators because of being elastically adjusted in position by the elastic element.

As described above, the embodiment has been described with reference to the specific matters such as the specific components, the limited embodiments, and the drawings, but these are provided to help the overall understanding. In addition, the present invention is not limited to the above-described embodiments, and various modifications and variations are possible from these descriptions by those skilled in the art to which the present invention pertains. Therefore, the spirit of the present invention should not be limited to the above-described embodiments, and not only the claims to be described later, but also all those with equivalent or equivalent modifications to the claims belongs to the scope of the spirit of the present invention.

The invention claimed is:

1. An apparatus for washing a handrail of an escalator, the apparatus comprising:
   a case configured to accommodate the handrail of the escalator and a washing part;
   a self-generation part disposed in the case to convert kinetic energy of the handrail of the escalator into electric energy;
   the washing part configured to wash the handrail of the escalator; and
   a control part configured to control the handrail of the escalator,
   wherein the washing part comprises a plurality of rollers,
   at least one roller rotates without power in a first direction that is opposite to a preset rotation direction of the handrail of the escalator by friction force generated by being in contact with a surface of the handrail of the escalator,
   other rollers rotate by rotational force of the at least one roller to disinfect and wash the handrail of the escalator while the other rollers rotate,
   a first sensor element configured to detect a rotation direction of the at least one roller is disposed at one side of the at least one roller, and
   when the first sensor element detects the rotation of the at least one roller in the first direction, the control part determines that an operation of the escalator is normal, when the first sensor element detects that the at least one roller does not rotate, the control part determines that the operation of the escalator is abnormal, and when the first sensor element detects that the at least one roller is rotating in a second direction that is opposite to the first direction, the control part determines that the operation of the escalator is abnormal.

2. The apparatus of claim 1, wherein the washing part comprises:
   a first roller rotating without the power in the first direction by the frictional force generated by being in contact with the surface of the handrail of the escalator;
   a second roller rotating in the second direction that is opposite to the first direction by the rotational force of the first roller to remove and disinfect foreign substances of the handrail by using a disinfectant solution sprayed onto the surface;
   a third roller rotating in the first direction by the rotational force of the first roller to wash the disinfectant solution adhering to the surface of the handrail; and
   a fourth roller rotating in the second direction by the rotational force of the first roller to rewash the disinfectant solution remaining on the surface of the handrail,
   wherein the first sensor element is disposed at one side of the first roller.

3. The apparatus of claim 2, wherein the washing part further comprises a frame configured to accommodate the first to fourth rollers, and
   a plurality of holes are sequentially formed in each of both side surfaces of the frame, and the first to fourth rollers are detached to the holes formed in both the side surfaces of the frame by a rotation shaft passing through each of the rollers, respectively.

4. The apparatus of claim 3, further comprising an elastic element disposed below the frame of the washing part so as to be connected to the frame,
   wherein the washing part moves elastically upward or downward by the elastic element so that the first to fourth rollers are in contact with the surface of the handrail of the escalator.

5. The apparatus of claim 4, further comprising:
   a first elastic element connected to a portion, at which the first roller is disposed, on the frame; and
   a second elastic element connected to a portion, at which each of the second to fourth rollers is disposed, on the frame,
   wherein the control part controls the first elastic element so that elastic force of the first elastic element corresponds to a first preset pressure that is set so that the first roller and the surface of the handrail of the escalator are in close contact with each other, and
   the control part controls the second elastic element so that the elastic force of the second elastic element corresponds to a second preset pressure set so that the second to fourth rollers and the surface of the handrail of the escalator are in contact with each other.

6. The apparatus of claim 5, wherein a second sensor element capable of detecting a concentration of the disinfectant solution remaining on the surface of the second roller is disposed on a portion of the surface of the first roller,
   the control part controls an amount of disinfectant solution sprayed onto the surface of the second roller, and
   the control part controls the amount of disinfectant solution sprayed onto the surface of the second roller, based on the concentration of the disinfectant solution detected by the second sensor element.

7. The apparatus of claim 6, wherein the self-generation part comprises a power generation element configured to convert the kinetic energy of the handrail of the escalator into the electric energy while rotating by the frictional force generated by being in contact with the surface of the handrail of the escalator;
   a charging element configured to store the electric energy generated by the power generation element; and
   a moving element capable of moving a position of the power generation element so that the power generation element is in contact with the surface of the handrail of the escalator,
   wherein the power generation element rotates about one axis by the moving element.

* * * * *